(12) United States Patent
Clegg et al.

(10) Patent No.: US 8,870,740 B2
(45) Date of Patent: Oct. 28, 2014

(54) SYSTEM AND METHOD FOR PROVIDING LIGHT THERAPY TO A SUBJECT

(75) Inventors: William Edwin Clegg, Gibsonia, PA (US); Michael Edward Colbaugh, Level Green, PA (US)

(73) Assignee: Koninklijke Philips N.V., Eindhoven (NL)

( * ) Notice: Subject to any disclaimer, the term of this patent is extended or adjusted under 35 U.S.C. 154(b) by 225 days.

(21) Appl. No.: 13/141,786

(22) PCT Filed: Dec. 9, 2009

(86) PCT No.: PCT/IB2009/055617
§ 371 (c)(1),
(2), (4) Date: Jun. 23, 2011

(87) PCT Pub. No.: WO2010/076707
PCT Pub. Date: Jul. 8, 2010

(65) Prior Publication Data
US 2011/0257467 A1 Oct. 20, 2011

Related U.S. Application Data

(60) Provisional application No. 61/141,274, filed on Dec. 30, 2008.

(51) Int. Cl.
*A61M 21/00* (2006.01)
*A61N 5/06* (2006.01)

(52) U.S. Cl.
CPC ...... *A61N 5/0618* (2013.01); *A61M 2021/0044* (2013.01); *A61N 2005/0648* (2013.01); *A61M 21/00* (2013.01)
USPC .............................................. 600/27; 607/88

(58) Field of Classification Search
USPC .................................. 600/26–28; 607/88–95
See application file for complete search history.

(56) References Cited

U.S. PATENT DOCUMENTS

| 4,790,031 A | * | 12/1988 | Duerer ............................... 2/439 |
| 4,858,609 A | | 8/1989 | Cole |
| 5,208,688 A | | 5/1993 | Fergason et al. |
| 5,304,212 A | * | 4/1994 | Czeisler et al. ................. 607/88 |
| 6,053,936 A | | 4/2000 | Koyama et al. |

(Continued)

FOREIGN PATENT DOCUMENTS

| JP | 05506950 A | 10/1993 |
| JP | 09213101 A | 8/1997 |

(Continued)

OTHER PUBLICATIONS https://www.lowbuelights.com, Bright-Eye Yellow Eyeglasses for Blocking-Out Blue and UV Light, Downloaded May 22, 2014, 5 pages.

(Continued)

*Primary Examiner* — Jacqueline Cheng
*Assistant Examiner* — Eileen Foley (57) ABSTRACT

A sleep mask is configured to provide light therapy to a subject. The sleep mask provides a comfortable delivery mechanism for the light therapy, and may deliver the light therapy to the subject while the subject is asleep, in the process of going to sleep, and/or waking from sleep. In one embodiment, the sleep mask includes one or more of a shield, a strap, a first lighting module, and/or a second lighting module.

21 Claims, 7 Drawing Sheets

(56) References Cited

U.S. PATENT DOCUMENTS

| | | | |
|---|---|---|---|
| 6,092,906 A | | 7/2000 | Olmstead |
| 8,356,895 B2* | | 1/2013 | Jackson et al. ........... 351/159.01 |
| 2002/0156508 A1 | | 10/2002 | Saathoff |
| 2004/0225340 A1 | | 11/2004 | Evans |
| 2008/0051858 A1* | | 2/2008 | Haber et al. .................... 607/88 |

FOREIGN PATENT DOCUMENTS

| | | | |
|---|---|---|---|
| JP | 2003144481 A | 5/2003 |
| WO | 9015639 A1 | 12/1990 |
| WO | 9747993 A1 | 12/1997 |

OTHER PUBLICATIONS http://www.flightgear.dk/flash.htm, Flightgear On-Line, Downloaded May 30, 2014, 6 pages.

http://en.wikipedia.org/wiki/rear-view_mirror, Downloaded May 30, 2014, 3 pages.

http:en.wikipedia.org/wiki/electrochromism, Downloaded May 30, 2014, 3 pages.

\* cited by examiner

SYSTEM AND METHOD FOR PROVIDING LIGHT THERAPY TO A SUBJECT

This patent application claims the priority benefit under 35 U.S.C. §119(e) of U.S. Provisional Application No. 61/141,274 filed on Dec. 30, 2008, the contents of which are herein incorporated by reference.

This application is related to U.S. patent application Ser. No. 61/141,273 entitled "SYSTEM AND METHOD FOR PROVIDING LIGHT THERAPY TO A SUBJECT," filed Dec. 30, 2008, and U.S. patent application Ser. No. 61/141,289 entitled "SYSTEM AND METHOD FOR ADMINISTERING LIGHT THERAPY," and filed Dec. 30, 2008, and U.S. patent application Ser. No. 61/141,292 entitled "SYSTEM AND METHOD FOR ADMINISTERING LIGHT THERAPY," filed Dec. 30, 2008, and U.S. patent application Ser. No. 61/141,295 entitled "SYSTEM AND METHOD FOR ADMINISTERING LIGHT THERAPY," filed Dec. 30, 2008, and U.S. patent application Ser. No. 61/152,028 entitled "SYSTEM AND METHOD FOR PROVIDING LIGHT THERAPY TO A SUBJECT," filed Feb. 12, 2009, which are hereby incorporated into this application in its entirety.

The invention relates to the provision of light therapy to a subject.

The direction of radiation on a subject to impact the Circadian rhythms and/or to address light deficient disorders of the subject are known. Generally, these treatments involve shining light directly towards a patient's eyes while the patient is awake to alleviate or cure light deficient disorders including Seasonal Affective Disorder (SAD), circadian sleep disorders and circadian disruptions associated with jet-lag, and shift-work.

There are two types of light therapy devices presently available. One type of device is large in size and floor or desk mountable. These devices include light sources of fluorescent bulbs or large arrays of light emitting diodes. Although they can be moved from one position to another, they are not generally portable and require a scheduled time period of being stationary during the active part of the day. In addition, the light source is quite fragile. The second kind of light therapy device is head mountable. These devices are formed as eyeglasses or visors. While they are portable, they are not generally accepted by patients for use in public because of their odd appearance when worn on the head. These devices generally lack features that enable them to be used while functioning during sleep. This second type of device mostly used focused or non-diffuse light sources to direct high luminance light towards the eyes.

Further, the lights are positioned to emit beams of light at the eyes of the patient while the patient is awake. This approach may impact the comfort of the treatment to the subject.

One aspect of the invention relates to a sleep mask configured to provide light therapy to a subject. In one embodiment, the sleep mask comprises a shield, one or more radiation sources, and one or more radiation diffusers. The shield is configured to cover the eyes of a subject wearing the sleep mask such that the shield provides a barrier between ambient radiation and the eyes of the subject. The one or more radiation sources are configured to emit radiation, and are carried by the shield. The one or more radiation diffusers are configured to receive radiation emitted by the one or more radiation sources, and to diffuse the radiation emitted by the one or more radiation sources to form one or more fields of radiation. The one or more radiation diffusers are carried by the shield, and are positioned on the shield such that the one or more fields of radiation are directed to the eyes of the subject wearing the sleep mask.

Another aspect of the invention relates to a method of providing light therapy to a subject. In one embodiment, the method comprises covering the eyes of a subject wearing the sleep mask such that a barrier is provided between ambient radiation and the eyes of the subject; emitting radiation between the eyes of the subject and the barrier; and diffusing the emitted radiation to form one or more fields of uniform radiation that are directed to the eyes of the subject wearing the sleep mask.

Another aspect of the invention relates to a mask configured to provide light therapy to a subject. In one embodiment, the system comprises means for covering the eyes of a subject wearing the mask such that a barrier is provided between ambient radiation and the eyes of the subject; means for emitting radiation between the eyes of the subject and the barrier; and means for diffusing the emitted radiation to form one or more fields of uniform radiation that are directed to the eyes of the subject wearing the mask.

Another aspect of the invention relates to a sleep mask configured to provide light therapy to a subject. In one embodiment, the sleep mask comprises a shield, one or more radiation sources, and one or more filters. The shield is configured to cover the eyes of a subject wearing the sleep mask such that the shield provides a barrier between ambient radiation and the eyes of the subject. The one or more radiation sources are configured to emit radiation that provides light therapy to the subject, and are carried by the shield such that radiation emitted by the one or more radiation sources is directed to the eyes of the subject. The one or more filters are disposed in one or more apertures in the shield, and are configured (i) to block ambient radiation that, if allowed to reach the eyes of the subject, would interfere with the light therapy provided to the subject by the radiation emitted by the one or more radiation sources, and (ii) to enabling ambient radiation to pass through the barrier formed by the shield that does not interfere with the light therapy provided to the subject by the radiation emitted by the one or more radiation sources.

Another aspect of the invention relates to a method of providing light therapy to a subject. In one embodiment, the method comprises covering the eyes of a subject by providing a barrier between ambient radiation and the eyes of the subject; emitting radiation between the eyes of the subject and the barrier; blocking ambient radiation at the barrier that, if allowed to reach the eyes of the subject, would interfere with the light therapy provided to the subject by the radiation emitted between the eyes of the subject and the barrier; and enabling ambient radiation to pass through the barrier that does not interfere with the light therapy provided to the subject by the radiation emitted between the eyes of the subject and the barrier.

Another aspect of the invention relates to a mask configured to provide light therapy to a subject. In one embodiment, the mask comprises means for covering the eyes of a subject by providing a barrier between ambient radiation and the eyes of the subject; means for emitting radiation between the eyes of the subject and the barrier; means for blocking ambient radiation at the barrier that, if allowed to reach the eyes of the subject, would interfere with the light therapy provided to the subject by the radiation emitted between the eyes of the subject and the barrier; and means for enabling ambient radiation to pass through the barrier that does not interfere with the light therapy provided to the subject by the radiation emitted between the eyes of the subject and the barrier.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. As used in the specification and in the claims, the singular form of "a", "an", and "the" include plural referents unless the context clearly dictates otherwise.

Figure 1:
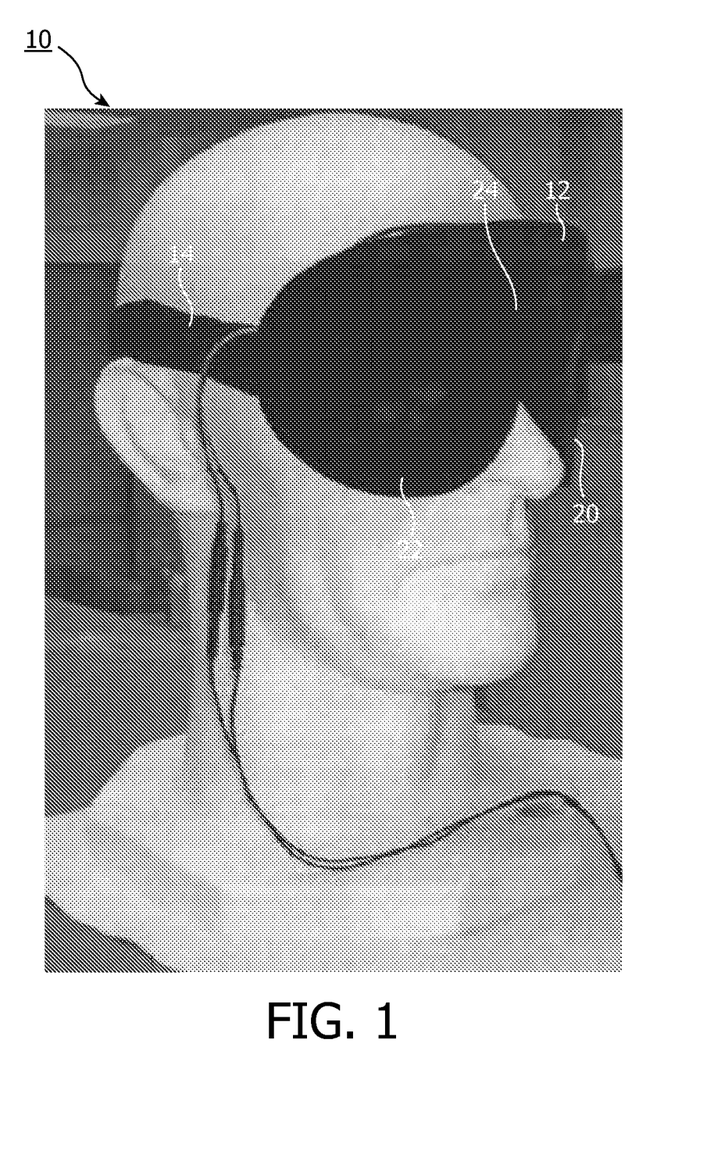
FIG. 1 illustrates a sleep mask configured to provide light therapy to a subject, in accordance with one or more embodiments of the invention.
Figure 2:
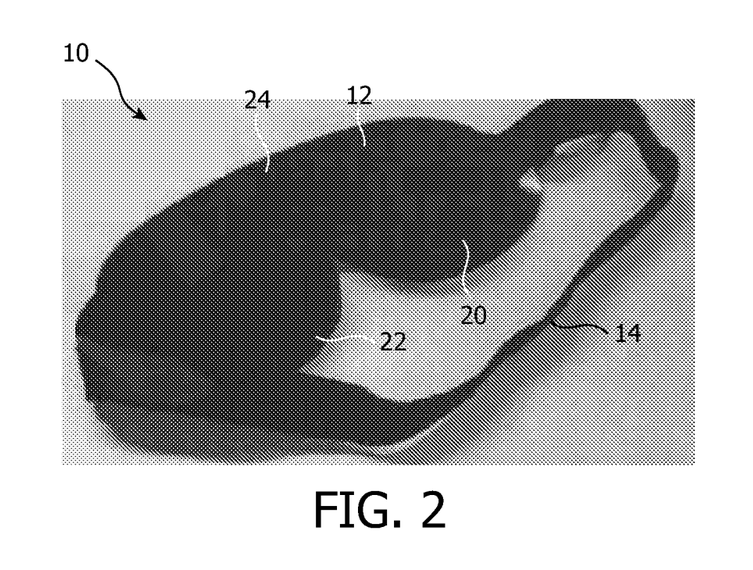
FIG. 2 illustrates a sleep mask configured to provide light therapy to a subject, in accordance with one or more embodiments of the invention.
Figure 3:
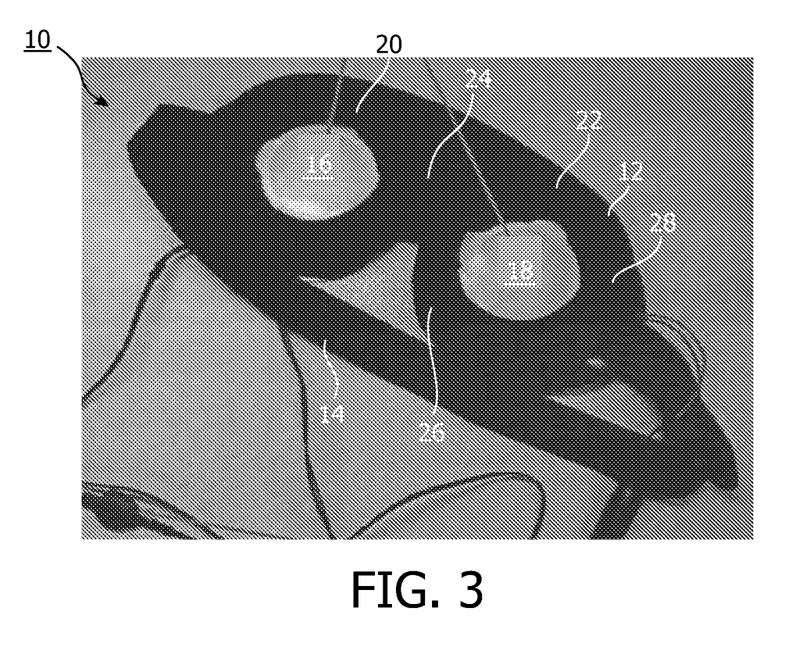
FIG. 3 illustrates a sleep mask configured to provide light therapy to a subject, in accordance with one or more embodiments of the invention.

FIGS. 1-3 illustrate a sleep mask 10 configured to provide light therapy to a subject. Sleep mask 10 may provide a comfortable delivery mechanism for the light therapy, and may deliver the light therapy to the subject while the subject is asleep, in the process of going to sleep, and/or waking from sleep. In one embodiment, sleep mask 10 includes one or more of a shield 12, a strap 14, a first lighting module 16, and/or a second lighting module 18.

As can be seen in FIG. 1, shield 12 is configured to cover the eyes of the subject wearing sleep mask 10. In one embodiment, shield 12 includes a first shield portion 20 and a second shield portion 22. First shield portion 20 is configured to cover a first eye of the subject. Second shield portion 22 is configured to cover a second eye of the subject. In order to comfortably cover the first eye and the second eye of the subject, first shield portion 20 and second shield portion 22 are substantially larger than the ocular openings of the eyes of the subject.

In one embodiment, first shield portion 20 and second shield portion 22 are joined by a connecting shield portion 24. Connecting shield portion 24 is configured to rest on at least a portion of the nose of the subject (e.g., across the bridge of the nose) when the subject is wearing sleep mask 10. In some instances (not shown), connecting shield portion 24 may be narrower or thicker than the embodiment depicted in FIGS. 1-3.

In one embodiment, shield 12 is formed from flexible materials. The flexibility of shield 12 may enhance the comfort of shield 12 to the subject. The side of shield 12 visible in FIG. 3 faces toward the subject during use. On this side, a base surface 26 substantially impermeable to liquids may be formed. For example, the impermeable base surface 26 may be formed by a flexible plastic material such as polycarbonate, polyester, and/or other materials. The impermeability of base surface 26 may protect electronic components of sleep mask 10 carried within shield 12 from moisture.

In one embodiment, shield 12 includes a cushioning layer 28 disposed on base surface 26. Cushioning layer 28 is formed from a soft, resilient material. For example, cushioning layer 28 may be formed from foam, fabric, fabric/foam laminate, and/or other materials. During use, cushioning layer 28 provides the innermost surface to the subject, and engages the face of the subject. As such, the softness of cushioning layer 28 provides a cushion for the face of the subject, and enhances the comfort of sleep mask 10 to the subject.

As will be appreciated from the foregoing and FIGS. 1-3, during use shield 12 provides a barrier between ambient radiation and the eyes of the subject. In one embodiment, shield 12 is opaque, and blocks ambient radiation (at least within the visible spectrum), thereby shielding the eyes of the subject from ambient radiation.

Strap 14 is configured to hold shield 12 in place on the subject. In the embodiments shown in FIGS. 1-3, strap 14 is attached to each of first shield portion 20 and second shield portion 22, and wraps around the head of the subject to hold sleep mask 10 in place on the head of the subject. Strap 14 may be adjustable in length (e.g., to accommodate different sized heads). Strap 14 may be formed from a resilient material (e.g., elastic) that stretches to accommodate the head of the user and holds shield 12 in place. It should be appreciated that the inclusion of strap 14 in the embodiments of sleep mask 10 illustrated in FIGS. 1-3 is not intended to be limiting. Other mechanisms for holding shield 12 in place on the subject are contemplated. For example, a more elaborate headgear may be implemented, an adhesive surface may be applied to shield 12 that removably adheres to the skin of the subject to hold shield 12 in place, a rigid or flexible frame (e.g., eyeglasses), and/or other mechanisms for holding shield 12 in place may be implemented.

Referring now to FIG. 3, first lighting module 16 and second lighting module 18 are mounted to first shield portion 20 and second shield portion 22, respectively, on the side of shield 12 that faces toward the face of the subject during use. First lighting module 16 and second lighting module 18 are backlit, and are configured to emit radiation onto the face of the subject on and/or about the eyes of the subject. The radiation emitted by first lighting module 16 and second lighting module 18 has a wavelength (or wavelengths) that have a therapeutic impact on the subject, when they are delivered in accordance with an effective light therapy plan. In some instances, the radiation emitted by first lighting module 16 and second lighting module 18 is directed towards the eyes of the subject in radiation fields having relatively uniform luminance as perceived by the subject. For example, in one embodiment, the luminance of the radiation emitted by first lighting module 16 and second lighting module 18 varies across the respective emitted fields by an amount that is less than or equal to about 100:1 for use with eyes open, and less than 10,000:1 for eyes-closed applications. The size of the uniform field of radiation formed by either first lighting module 16 or second lighting module 18 may correspond to the size of the eye of the subject.

Figure 4A:
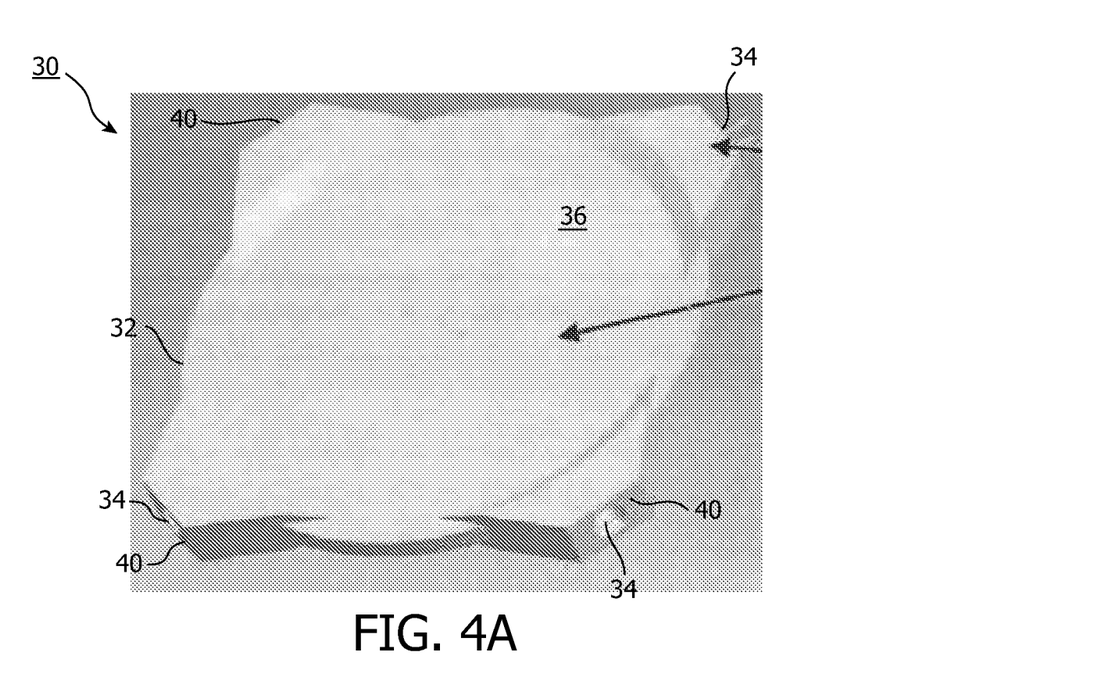
FIG. 4A illustrates a lighting module, according to one or more embodiments of the invention.
Figure 4B:
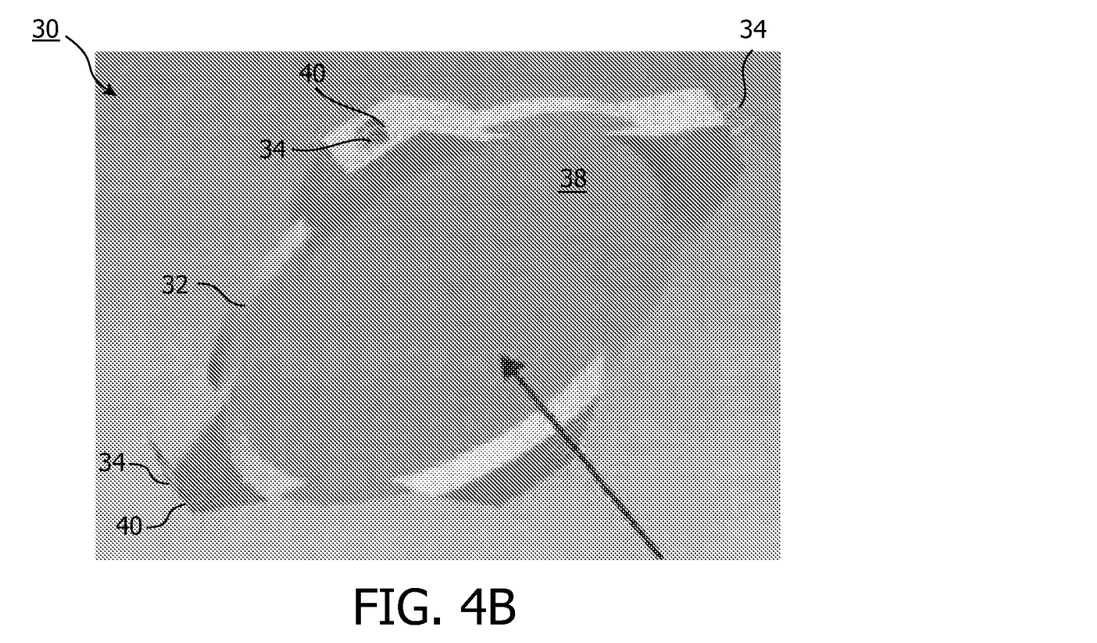
FIG. 4B illustrates a lighting module, according to one or more embodiments of the invention.

FIGS. 4A and 4B illustrate a lighting module 30, in accordance with one embodiment of the invention. Lighting module 30, in some instances, may be implemented as first lighting module 16 and/or second lighting module 18 in the embodiment of sleep mask 10 depicted in FIGS. 1-3. In the embodiment of lighting module 30 illustrated in FIGS. 4A and 4B, lighting module 30 includes a waveguide 32 and one or more radiation sources 34.

Waveguide 32 is configured to receive radiation emitted by radiation sources 34, and to direct at least some of the received radiation on to the face of the subject on or about the eyes. Waveguide 32 has a front side 36 and a back side 38 that is on the opposite side of waveguide 32 from front side 36. During use, front side 36 (shown in FIG. 4A) faces toward the face of the subject, and radiation emitted from lighting module 30 is emitted from front side 36. In one embodiment, some or all of back side 38 (shown in FIG. 4B) is coated with a reflective surface that keeps radiation that is inside of waveguide 32 from leaving waveguide 32 at back side 38.

In one embodiment, waveguide 32 is formed from a material (or materials) and/or with a structure (or structures) that diffuse radiation propagating therein. For example, waveguide 32 may be formed from one or more of silica glass, acrylic, polycarbonate, and/or other materials. The diffusion of radiation within waveguide 32 ensures that the fields of radiation emitted from front side 36 of lighting module 30 will have the appropriate uniformity in illuminance. In addition to diffusing radiation traveling therein, waveguide 32 is formed to direct radiation emitted from radiation sources 34 onto the face of the subject at the appropriate location (e.g., on or about the eyes).

As can be seen in FIGS. 4A and 4B, in one embodiment, waveguide 32 includes one or more source ports 40. Source ports 40 are disposed at the periphery of waveguide 32, and are configured to enable radiation sources 34 to be mounted on waveguide 32. In the embodiment shown, source ports 40 include cavities formed in waveguide 32 into which radiation sources 34 can be inserted. By mounting radiation sources 34 to waveguide 32, the radiation emitted by radiation sources 34 is immediately received by waveguide 32. This may reduce light loss within lighting module 30. However, it will be appreciated that this is not intended to be limiting and that in some embodiments, radiation sources 34 may be disposed within lighting module 30 separately from waveguide 32.

Figure 5:
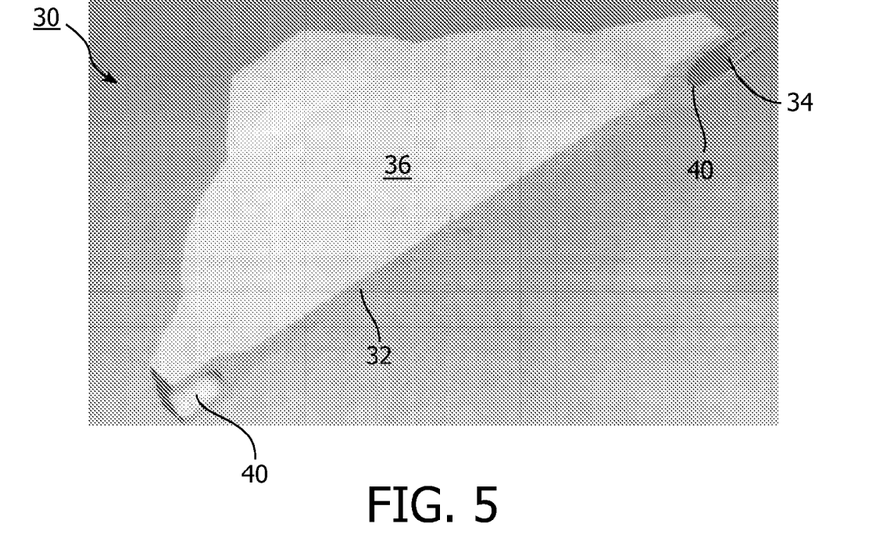
FIG. 5 illustrates a lighting module, according to one or more embodiments of the invention.

FIG. 5 is a sectional view of waveguide 32 that shows the formation of source ports 40 and the mounting of radiation sources 34 therein. In the embodiment of lighting module 30 illustrated in FIG. 5, radiation sources 34 are light emitting diodes ("LEDs"), or other directional radiation source that tend to emit radiation in a directed, relatively narrow beam. Radiation sources 34 are configured to emit radiation having a wavelength (or wavelengths) that have a therapeutic benefit to the subject, provided the radiation is administered to the subject in accordance with an appropriate light therapy plan.

Radiation sources 34, in the embodiment shown in FIG. 5, are mounted to waveguide 32 in a "side firing" configuration.

As used herein, a "side firing" configuration refers to a configuration of a radiation source 34 wherein the source emits a beam of radiation in a direction that is transverse to the direction along which the field of radiation directed to the face of the user is emitted from lighting module 30.

In the side firing configuration of radiation sources 34 depicted in FIG. 5, radiation sources 34 are arranged in lighting module 30 to emit directional, relatively narrow beams of radiation along optical paths that are askew from the eye of the subject (during use). By virtue of the diffusive and/or reflective materials used to form waveguide 32, waveguide 32 receives the radiation emitted by radiation sources 34 along the optical paths that are askew from the eye of the subject, diffuses the radiation into a uniform field of radiation, and guides the uniform field of radiation onto the eye of the subject.

The illustration in FIGS. 4 and 5 of embodiments in which radiation sources 34 include side firing LEDs is not intended to be limiting. The backlighting of lighting module 30 may be accomplished using other sources and/or configurations. For example, other types of light emitters may be implemented. As another example, in one embodiment, radiation sources 34 are not provided in a side firing configuration, but instead are disposed to emit radiation into waveguide 32 at back side 38. In this, and other configurations, waveguide 32 still diffuses the light to ensure that the radiation emitted by lighting module 30 onto the face of the subject has the appropriate uniformity.

Furthermore, the waveguide may have any of its surfaces imprinted with lens or mirror gratings (e.g. Fresnel lens structures) to reflect and/or direct the light energy as desired to the surface of the eye or eyelid. Parts of one or more surfaces may be imprinted with gratings. Parts of one or more surfaces may use reflective, translucent, diffusing, opaque reflective, or opaque absorptive areas designed to achieve a desired uniformity or directivity of the light field. The waveguide may employ color transmissive/absorptive/reflective filter surfaces or films to prevent undesired wavelengths from emanating from or passing through the waveguide.

Figure 6:
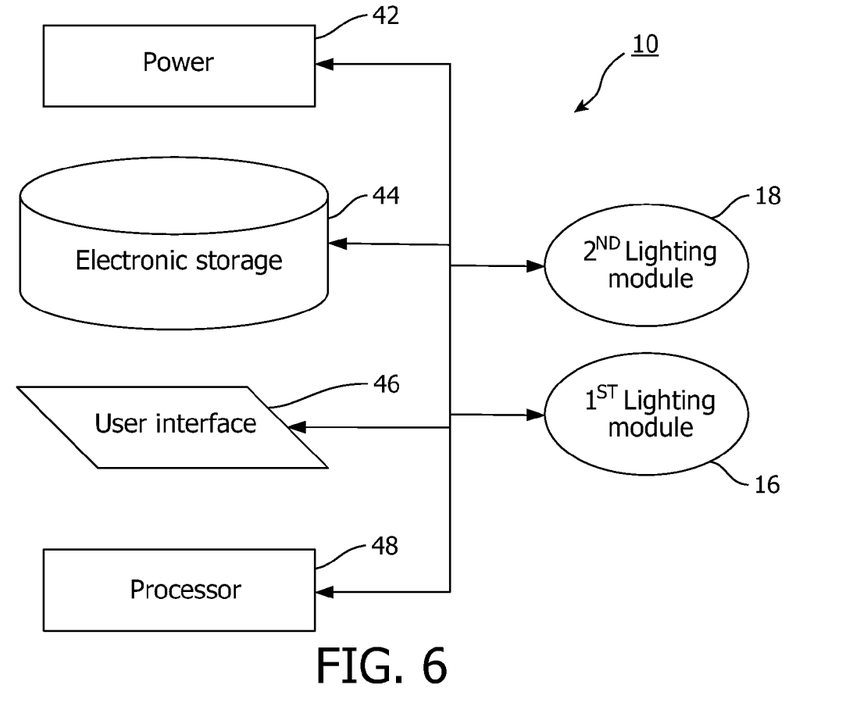
FIG. 6 illustrates a sleep mask configured to provide light therapy to a subject, in accordance with one or more embodiments of the invention.

FIG. 6 is a schematic illustration of sleep mask 10, in accordance with one or more embodiments of the invention. As can be seen in FIG. 6, in addition to one or more of the components shown in FIGS. 1-3 and described above, sleep mask 10 may include one or both of a power source 42, electronic storage 44, a user interface 46, and/or a processor 48. In one embodiment, one or more of power source 42, user interface 46, and/or processor 48 are carried on shield 12 and/or strap 14 of sleep mask 10. In this embodiment, one or more of power source 42, electronic storage 44, user interface 46, and/or processor 48 may be removably attached to shield 12 and/or strap 14, and may be disconnectable from the rest of sleep mask 10. This will enable power source 42, electronic storage 44, user interface 46, and/or processor 48 to be removed from a given shield 12 and/or strap 14, and attached to another shield 12 and/or strap 14, which may be beneficial if shield 12 and/or strap 14 degrade over time and/or with usage and must be replaced. Similarly, in one embodiment, first lighting module 16 and second lighting module 18 are also removable/replaceable on shield 12. Power source 42, electronic storage 44, user interface 46, and/or processor 48 may control operation the radiation sources associated with first lighting module 16 and/or second lighting module 18, as is discussed below.

Power source 42 provides the power necessary to operate the radiation sources associated with first lighting module 16 and second lighting module 18, and/or to power electronic storage 44, user interface 46, and/or processor 48. Power source 42 may include a portable source of power (e.g., a battery, a fuel cell, etc.), and/or a non-portable source of power (e.g., a wall socket, a large generator, etc.). In one embodiment, power source 42 includes a portable power source that is rechargeable. In one embodiment, power source 42 includes both a portable and non-portable source of power, and the subject is able to select which source of power should be used to provide power to sleep mask 10.

In one embodiment, electronic storage 44 comprises electronic storage media that electronically stores information. The electronically storage media of electronic storage 44 may include one or both of system storage that is provided integrally (i.e., substantially non-removable) with sleep mask 10 and/or removable storage that is removably connectable to sleep mask 10 via, for example, a port (e.g., a USB port, a firewire port, etc.) or a drive (e.g., a disk drive, etc.). Electronic storage 44 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 44 may store software algorithms, information determined by processor 48, information received via user interface 46, and/or other information that enables sleep mask 10 to function properly. Electronic storage 44 may include media provided as a separate component within sleep mask 10. Electronic storage 44 may include media provided integrally with one or more other components of sleep mask 10 (e.g., processor 48).

User interface 46 is configured to provide an interface between sleep mask 10 and the subject (and/or a caregiver) through which the subject (and/or a caregiver) may provide information to and receive information from sleep mask 10. This enables data, results, and/or instructions and any other communicable items, collectively referred to as "information," to be communicated between the subject and processor 48. Examples of interface devices suitable for inclusion in user interface 46 include a keypad, buttons, switches, a keyboard, knobs, levers, a display screen, a touch screen, speakers, a microphone, an indicator light, an audible alarm, and a printer. In one embodiment, the functionality of which is discussed further below, user interface 46 actually includes a plurality of separate interfaces, including one interface that is carried on sleep mask 10, and a separate interface provided to view and/or manage stored information that has been retrieved from sleep mask 10 (e.g., provided by a host computer to which information from sleep mask 10 can be received).

It is to be understood that other communication techniques, either hard-wired or wireless, are also contemplated by the present invention as user interface 46. For example, the present invention contemplates that user interface 46 may be integrated with a removable storage interface provided by electronic storage 44. In this example, information may be loaded into sleep mask 10 from removable storage (e.g., a smart card, a flash drive, a removable disk, etc.) that enables the user(s) to customize the implementation of sleep mask 10. Other exemplary input devices and techniques adapted for use with sleep mask 10 as user interface 46 include, but are not limited to, an RS-232 port, RF link, an IR link, modem (telephone, cable or other). In short, any technique for communicating information with sleep mask 10 is contemplated by the present invention as user interface 46.

Processor 48 is configured to provide information processing and/or system control capabilities in sleep mask 10. As such, processor 48 may include one or more of a digital processor, an analog processor, a digital circuit designed to process information, an analog circuit designed to process information, a state machine, and/or other mechanisms for electronically processing information. In order to provide the functionality attributed to processor 48 herein, processor 48 may execute one or more modules. The one or more modules may be implemented in software; hardware; firmware; some combination of software, hardware, and/or firmware; and/or otherwise implemented. Although processor 48 is shown in FIG. 1 as a single entity, this is for illustrative purposes only. In some implementations, processor 48 may include a plurality of processing units. These processing units may be physically located within the same device (e.g., sleep mask 10), or processor 48 may represent processing functionality of a plurality of devices operating in coordination.

In one embodiment, processor 48 controls first lighting module 16 and second lighting module 18 in accordance with a predetermined light therapy algorithm. The predetermined light therapy algorithm may dictate the timing, the intensity, and/or the wavelength of the radiation emitted by first lighting module 16 and second lighting module 18 toward the face of the subject on or about the eyes of the subject. In one embodiment, the predetermined light therapy algorithm is stored in electronic storage 44, and is provided to processor 48 for execution via control of first lighting module 16 and second lighting module 18. In some instances, one or more aspects of the predetermined light therapy algorithm may be adjusted or customized for the subject. Adjustments and/or customizations to the predetermined light therapy algorithm may be input to sleep mask 10 via user interface 46. In one embodiment, electronic storage 44 stores a plurality of different predetermined light therapy algorithms, and the subject (and/or a caregiver) select the predetermined light therapy algorithm that is appropriate for the subject via user interface 46.

As was mentioned above, in one embodiment, the predetermined light therapy algorithm may dictate the timing of the administration of radiation to the subject by sleep mask 10. As such, in this embodiment, processor 48 includes a clock. The clock may be capable of monitoring elapsed time from a given event and/or of monitoring the time of day. The subject (and/or a caregiver) may be enabled to correct the time of day generated by the clock of processor 48 via, for example, user interface 46.

Figure 7:
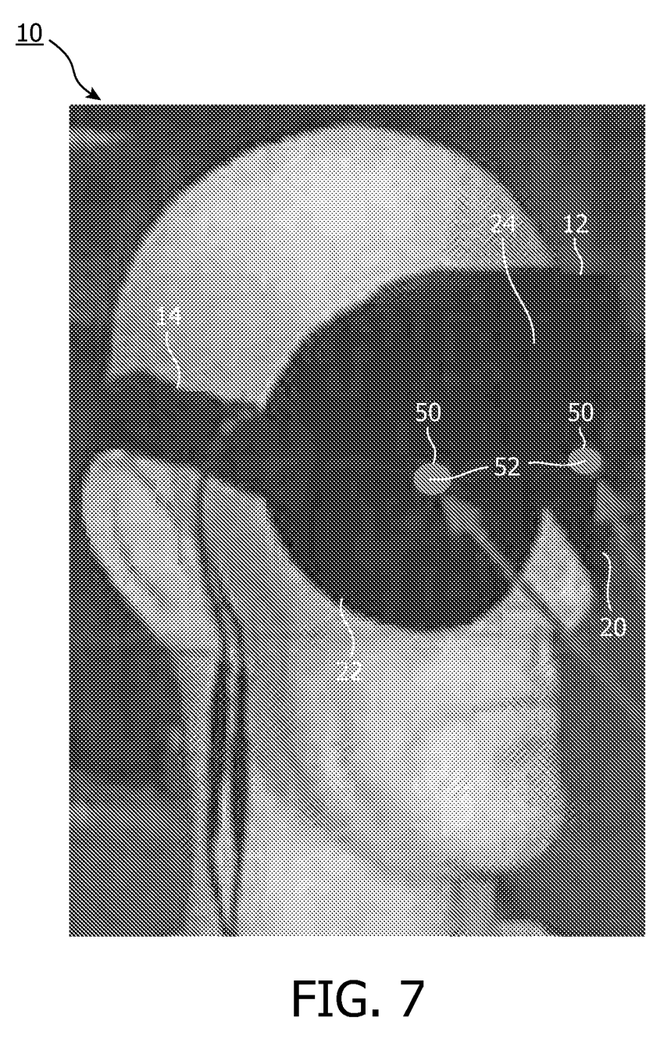
FIG. 7 illustrates a sleep mask configured to provide light therapy to a subject, in accordance with one or more embodiments of the invention.

FIG. 7 illustrates an embodiment of sleep mask 10, in which one or more apertures 50 are formed in shield 12 to enable the subject to see through shield 12. In one embodiment sleep mask 10 is designed to be worn primarily as the subject is asleep, falling asleep, or waking from sleep. However, there may still be times when the subject would like to be able to see (at least in some limited fashion) while wearing sleep mask 10. As such, apertures 50 may provide some limited sight to the subject.

It is known that receipt of radiation at some wavelengths has an impact on the Circadian rhythms of subjects. As such, if sleep mask 10 is providing radiation to the subject at these wavelengths at predetermined intensities and/or times in accordance with a predetermined light therapy algorithm, the reception of such radiation (e.g., in ambient light) at times that are out of synch with the administration of radiation according to the predetermined light therapy algorithm may have a deleterious impact on the therapeutic benefits received by the subject from use of sleep mask 10.

In order to reduce the potentially deleterious impact of ambient light that becomes incident on the eyes of the subject, in one embodiment, sleep mask 10 includes one or more filters 52 disposed in apertures 50. Filters 52 are configured to block ambient radiation that, if allowed to reach the eyes of the subject, would interfere with the light therapy provided to the subject by sleep mask 10. Filters 52 are further configured to enable ambient radiation to pass through the barrier formed by shield 12 that does not interfere with the light therapy provided to subject by sleep mask 10.

For example, in one embodiment, filters 52 comprise passive filters that block ambient radiation having a wavelength in a predetermined wavelength range. The predetermined wavelength range is the range of wavelengths at which ambient light would interfere with the light therapy provided by sleep mask 10. By way of non-limiting example, in one embodiment, the predetermined wavelength range includes wavelengths shorter than or equal to about 580 nm. In one embodiment, the predetermined wavelength range includes wavelengths between about 580 nm and about 410 nm. Blocking light in the predetermined wavelength, while reducing the deleterious impact of ambient light on the light therapy received by the subject from sleep mask 10, will still allow the subject to see through apertures 50. For example, the portion of the visible spectrum outside of the predetermined wavelength (e.g., >580 nm) will pass through filters 52, thereby enabling the subject to see.

Figure 8:
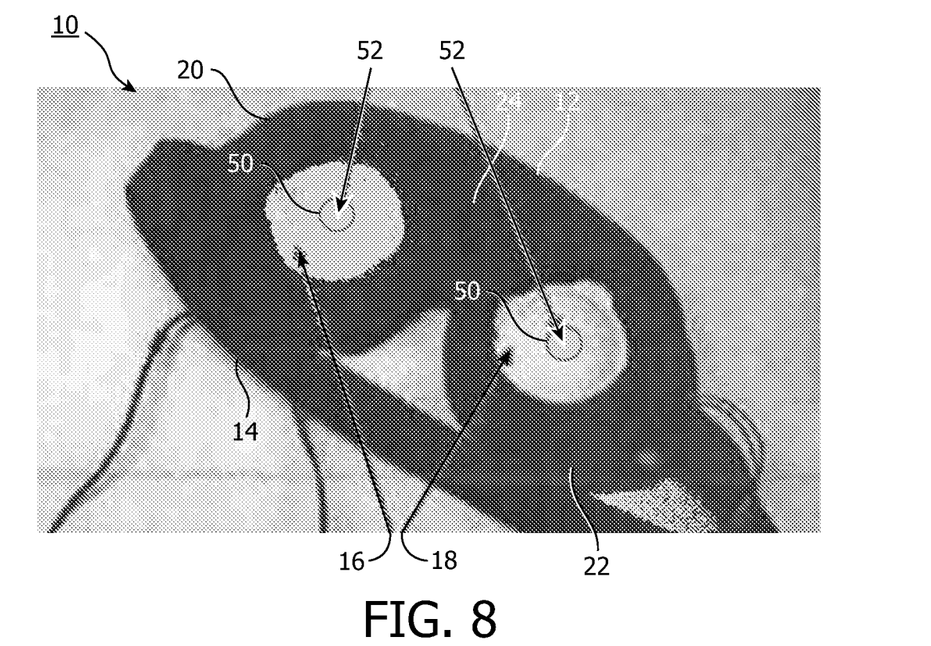
FIG. 8 illustrates a sleep mask configured to provide light therapy to a subject, in accordance with one or more embodiments of the invention.

In the embodiment illustrated in FIG. 7, apertures 50 are formed in first shield portion 20 and second shield portion 22 over a portion of the eye of the subject. FIG. 8, illustrates the inner side of the embodiment of sleep mask 10 shown in FIG. 7. As can be seen in FIG. 8, apertures 50 are formed not only in shield 12, but also in first lighting module 16 and second lighting module 18, to permit the subject to see through shield 12 via apertures 50 and filters 52.

Figure 9:
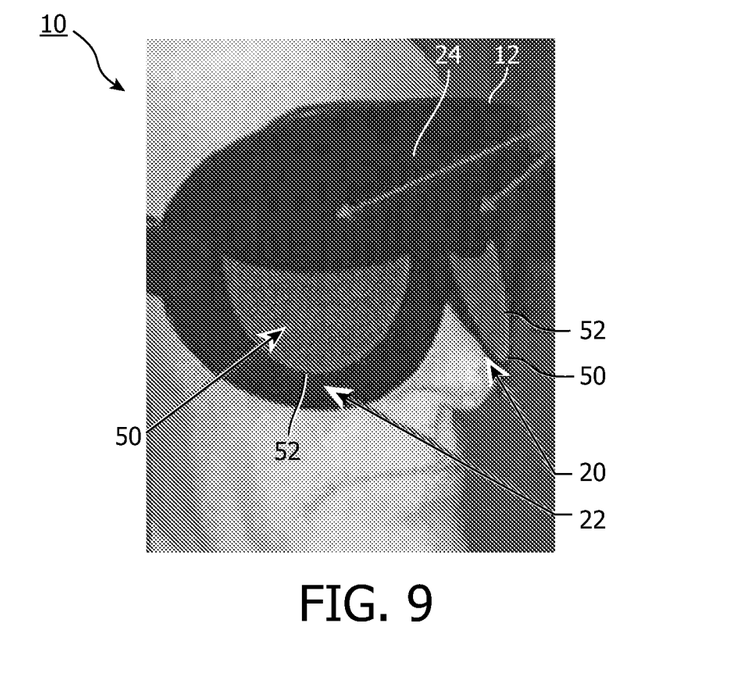
FIG. 9 illustrates a sleep mask configured to provide light therapy to a subject, in accordance with one or more embodiments of the invention.

FIG. 9 illustrates another embodiment of sleep mask 10. In the embodiment of sleep mask 10 shown in FIG. 9, apertures 50, rather than being formed as small, relatively central openings in shield 12, are formed as larger openings in the lower section of shield 12. In this embodiment, although not visible in FIG. 9, first lighting module 16 and second lighting module 18 may be positioned just above apertures 50 on the inner side of shield 12. Optionally, first lighting module 16 and second lighting module 18 may also provide an additional arch of the lighting module's body that circles under the window opening to project light towards the eyes as desired (e.g. provide more illumination to the lower portion of the eye).

Figure 10:
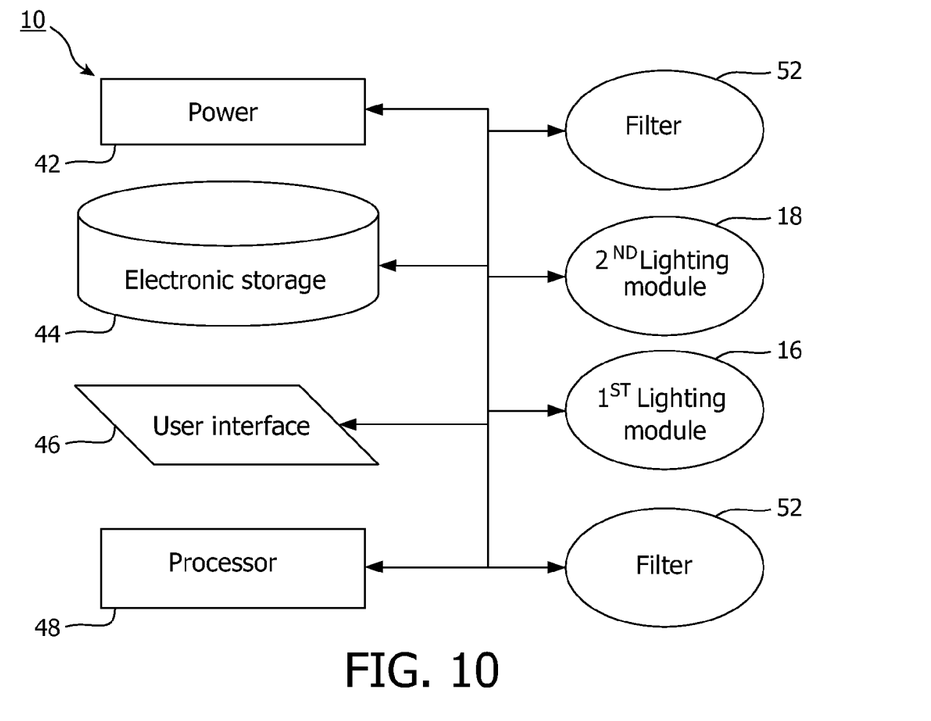
FIG. 10 illustrates a sleep mask configured to provide light therapy to a subject, in accordance with one or more embodiments of the invention.

FIG. 10 is a schematic illustration of an embodiment of sleep mask 10. In the embodiment of sleep mask 10 illustrated in FIG. 10, filters 52 have transmission characteristics that can be selectively controlled. For example, filters 52 may be controlled to block or transmit radiation at one or more predetermined wavelengths (e.g., between about 410 nm and about 580 nm, below about 580 nm, etc.), to block or transmit all (or substantially all) visible wavelengths, and/or otherwise controlled.

As can be seen in FIG. 10, filters 52 are in operative communication with power source 42 and processor 48. As such, filters 52 are powered by power source 42, and are controlled by processor 48. Processor 48 may control filters 52 in accordance with timing dictated by the same predetermined light therapy algorithm used by processor 48 to control the emission of radiation by first lighting module 16 and second lighting module 18. In instances in which processor 48 controls filters 52 to block all (or substantially all) visible wavelengths, user interface 46 may include an override control that enables the subject to override the predetermined light therapy algorithm so that processor 48 controls filters 52 to unblock apertures 50, at least temporarily.

Figure 11:
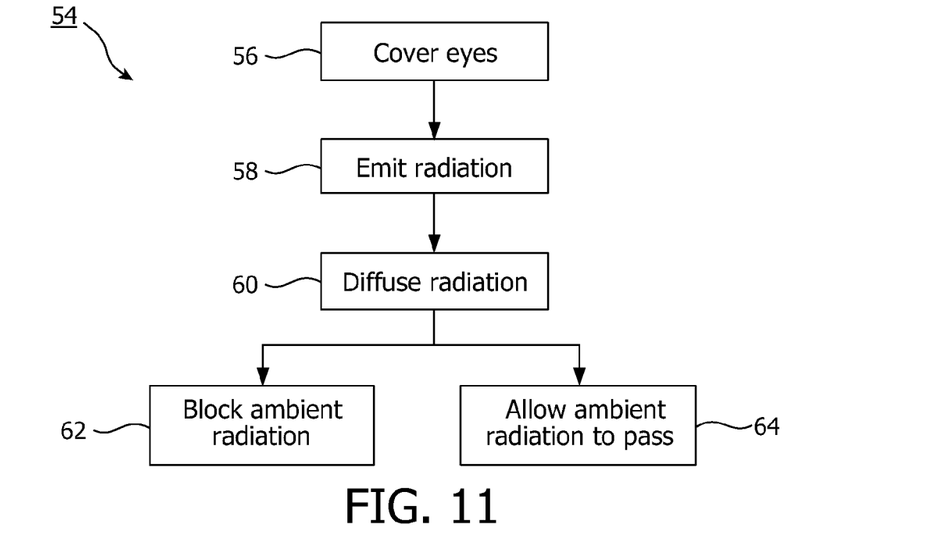
FIG. 11 illustrates a method of providing light therapy to a subject, in accordance with one or more embodiments of the invention.

FIG. 11 illustrates a method 54 of providing light therapy to a subject. The operations of method 54 presented below are intended to be illustrative. In some embodiments, method 54 may be accomplished with one or more additional operations not described, and/or without one or more of the operations discussed. Additionally, the order in which the operations of method 54 are illustrated in FIG. 11 and described below is not intended to be limiting. In some embodiments, one or more of the method 54 may be implemented in a sleep mask that is the same as or similar to sleep mask 10 (shown in FIGS. 1-10, and described above). However, in some embodiments, method 54 is implemented in systems and/or contexts that are different than those described above with respect to sleep mask 10.

At an operation 56, the eyes of the subject are covered by providing a barrier between ambient radiation and the eyes of the subject. In one embodiment, operation 56 is accomplished via a shield that is the same as or similar to sleep mask 10 (shown in FIGS. 1-3 and 7-9, and described above).

At an operation 58, radiation is emitted between the eyes of the subject and the barrier provided at operation 56. The radiation may be emitted in accordance with a predetermined light therapy algorithm. To emit the radiation in accordance with the predetermined light therapy algorithm, the timing, intensity, wavelength and/or other parameters of the radiation may be controlled automatically and/or manually. In one embodiment, the emission of radiation at operation 58 is accomplished by a lighting module that is the same as or similar to first lighting module 16, second lighting module 18 (shown in FIGS. 3, 6, 8, and 10, and described above) and/or lighting module 30 (shown in FIGS. 4A, 4B, and 5, and described above).

At an operation 60, the radiation emitted at operation 58 is diffused to form one or more fields of uniform radiation that are directed to the eyes of the subject wearing the sleep mask. In one embodiment, the diffusion of radiation at operation 60 is accomplished by a lighting module that is the same as or similar to first lighting module 16, second lighting module 18 (shown in FIGS. 3, 6, 8, and 10, and described above) and/or lighting module 30 (shown in FIGS. 4A, 4B, and 5, and described above).

At an operation 62, ambient radiation is blocked at the barrier which, if allowed to reach the eyes of the subject, would interfere with the light therapy provided to the subject by the radiation emitted at operation 58. In one embodiment, operation 62 is performed by one or more filters that are the same as or similar to filters 52 (shown in FIGS. 7-10 and described above).

At an operation 64, ambient radiation that does not interfere with the light therapy provided to the subject by the radiation emitted at operation 58 is allowed to pass through the barrier. In one embodiment, operation 64 is performed by one or more filters that are the same as or similar to filters 52 (shown in FIGS. 7-10 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A sleep mask configured to provide light therapy to a subject to impact circadian rhythms and/or light deficient disorders of the subject, the sleep mask comprising:

a shield configured to cover the eyes of a subject wearing the sleep mask such that the shield blocks ambient radiation from the eyes of the subject, the shield having one or more apertures configured to allow ambient light to reach the eyes of the subject;

one or more radiation sources configured to emit radiation that provides light therapy to the subject, emitting radiation that provides light therapy including emitting radiation having first wavelengths during a first portion of the light therapy and emitting radiation having second wavelengths during a second portion of the light therapy, the one or more radiation sources being carried by the shield such that radiation emitted by the one or more radiation sources is directed to the eyes of the subject; and one or more filters disposed in the one or more apertures in the shield, the one or more filters being configured:

(i) to block ambient radiation at wavelengths that, if allowed to reach the eyes of the subject, would interfere with the light therapy provided to the subject by the radiation emitted by the one or more radiation sources, and (ii) to enable ambient radiation to pass through the one or more apertures at wavelengths that do not interfere with the light therapy provided to the subject by the radiation emitted by the one or more radiation sources, wherein interfering with the light therapy includes reducing the impact of the light therapy on the circadian rhythms and/or light deficient disorders of the subject, wherein ambient radiation having third wavelengths reduces the impact of the light therapy on the circadian rhythms and/or light deficient disorders of the subject during the first portion of light therapy and does not reduce the impact of the light therapy on the circadian rhythms and/or light deficient disorders of the subject during the second portion of light therapy, and wherein the one or more filters block the ambient radiation having third wavelengths during the first portion of light therapy and enable the ambient radiation having third wavelengths to pass through the one or more apertures during the second portion of the light therapy.

2. The sleep mask of claim 1, wherein the one or more filters are configured (i) to block ambient radiation at wavelengths across the visible spectrum that, if allowed to reach the eyes of the subject, would interfere with the light therapy provided to the subject by the radiation emitted by the one or more radiation sources, and (ii) to enable ambient radiation to pass through the one or more apertures at wavelengths across the visible spectrum that do not interfere with the light therapy provided to the subject by the radiation emitted by the one or more radiation sources.

3. The sleep mask of claim 2, wherein the one or more filters are configured to enable ambient radiation to pass through the one or more apertures at wavelengths greater than about 580 nm during the first portion and the second portion of the light therapy.

4. The sleep mask of claim 1, further comprising a processor connected to the one or more radiation sources, and configured to control the one or more radiation sources and the one or more filters in accordance with a predetermined light therapy algorithm.

5. A sleep mask configured to provide light therapy to a subject to impact circadian rhythms and/or light deficient disorders of the subject, the sleep mask comprising:

a shield configured to cover the eyes of a subject wearing the sleep mask such that the shield blocks ambient radiation from the eyes of the subject, the shield having one or more apertures configured to allow ambient light to reach the eyes of the subject;

one or more radiation sources configured to emit radiation that provides light therapy to the subject, emitting radiation that provides light therapy including emitting radiation having first wavelengths during a first portion of the light therapy and emitting radiation having second wavelengths during a second portion of the light therapy, the one or more radiation sources being carried by the shield such that radiation emitted by the one or more radiation sources is directed to the eyes of the subject;

one or more filters disposed in the one or more apertures in the shield, the one or more filters being configured (i) to block ambient radiation at wavelengths that, if allowed to reach the eyes of the subject, would interfere with the light therapy provided to the subject by the radiation emitted by the one or more radiation sources, and (ii) to enable ambient radiation to pass through the one or more apertures at wavelengths that do not interfere with the light therapy provided to the subject by the radiation emitted by the one or more radiation sources;

wherein interfering with the light therapy includes reducing the impact of the light therapy on the circadian rhythms and/or light deficient disorders of the subject; the ambient radiation having third wavelengths that reduce the impact of the light therapy on the circadian rhythms and/or light deficient disorders of the subject during the first portion of light therapy and do not reduce the impact of the light therapy on the circadian rhythms and/or light deficient disorders of the subject during the second portion of light therapy; and a processor connected to the one or more radiation sources and configured to control the one or more radiation sources in accordance with a predetermined light therapy algorithm, wherein the processor is further configured to control the transmission characteristics of the one or more filters in accordance with the predetermined light therapy algorithm such that the one or more filters block the ambient radiation having third wavelengths during the first portion of the light therapy and enable the ambient radiation having third wavelengths to pass through the one or more apertures during the second portion of the light therapy.

6. The sleep mask of claim 5, wherein the processor is configured to control the transmission characteristics of the one or more filters by varying the transmission of the one or more filters for radiation within a predetermined wavelength range.

7. The sleep mask of claim 5, wherein the processor is configured to control the transmission characteristics of the one or more filters by varying the transmission of the one or more filters for radiation across the visible spectrum.

8. A method of providing light therapy to a subject to impact circadian rhythms and/or light deficient disorders of the subject, the method comprising:

covering the eyes of a subject with a shield such that ambient radiation is blocked from the eyes of the subject, the shield having one or more apertures configured to allow ambient light to reach the eyes of the subject;

emitting radiation between the eyes of the subject and the shield that provides light therapy to the subject, wherein emitting radiation that provides light therapy includes emitting radiation having first wavelengths during a first portion of the light therapy and emitting radiation having second wavelengths during a second portion of the light therapy;

blocking ambient radiation, at the one or more apertures in the shield, having wavelengths that, if allowed to reach the eyes of the subject, would interfere with the light therapy provided to the subject by the radiation emitted between the eyes of the subject and the shield; and enabling ambient radiation to pass through the one or more apertures in the shield having wavelengths that do not interfere with the light therapy provided to the subject by the radiation emitted between the eyes of the subject and the shield, wherein interfering with the light therapy includes reducing the impact of the light therapy on the circadian rhythms and/or light deficient disorders of the subject, wherein ambient radiation having third wavelengths reduces the impact of the light therapy on the circadian rhythms and/or light deficient disorders of the subject during the first portion of light therapy and does not reduce the impact of the light therapy on the therapy, and wherein the ambient radiation having third wavelengths is blocked during the first portion of light therapy and enabled to pass through the one or more apertures during the second portion of the light therapy.

9. The method of claim 8, wherein blocking ambient radiation at the one or more apertures in the shield that, if allowed to reach the eyes of the subject, would interfere with the light therapy provided to the subject by the radiation emitted between the eyes of the subject and the shield comprises blocking ambient radiation at wavelengths across the visible spectrum that, if allowed to reach the eyes of the subject, would interfere with the light therapy provided to the subject by the radiation emitted between the eyes of the subject and the shield, and wherein enabling ambient radiation to pass through the one or more apertures in the shield that does not interfere with the light therapy provided to the subject by the radiation emitted between the eyes of the subject and the shield comprises enabling ambient radiation to pass through the shield at wavelengths across the visible spectrum that do not interfere with the light therapy provided to the subject by the radiation emitted between the eyes of the subject and the shield.

10. The method of claim 9, wherein ambient radiation that, if allowed to reach the eyes of the subject, would interfere with the light therapy provided to the subject by the radiation emitted between the eyes of the subject and the shield comprises ambient radiation having a wavelength at or above about 580 nm, and wherein ambient radiation that does not interfere with the light therapy provided to the subject by the radiation emitted between the eyes of the subject and the shield comprises ambient radiation having a wavelength at or below about 580 nm.

11. The method of claim 8, further comprising controlling the emission of radiation between the shield and the eyes of the subject, the blocking of the ambient radiation at the apertures, and the enabling of the ambient radiation to pass through the apertures in accordance with a predetermined light therapy algorithm.

12. A method of providing light therapy to a subject to impact circadian rhythms and/or light deficient disorders of the subject, the method comprising:

covering the eyes of a subject with a shield such that ambient radiation is blocked from the eyes of the subject, the shield having one or more apertures configured to allow ambient light to reach the eyes of the subject;

emitting radiation between the eyes of the subject and the shield that provides light therapy to the subject, wherein emitting radiation that provides light therapy includes emitting radiation having first wavelengths during a first portion of the light therapy and emitting radiation having second wavelengths during a second portion of the light therapy;

blocking ambient radiation, at the one or more apertures in the shield, having wavelengths that, if allowed to reach the eyes of the subject, would interfere with the light therapy provided to the subject by the radiation emitted between the eyes of the subject and the shield;

enabling ambient radiation to pass through the one or more apertures in the shield having wavelengths that do not interfere with the light therapy provided to the subject by the radiation emitted between the eyes of the subject and the shield;

controlling the emission of radiation between the shield and the eyes of the subject in accordance with a predetermined light therapy algorithm; and controlling transmission characteristics of one or more filters disposed in the one or more apertures in the shield in accordance with the predetermined light therapy algorithm to accomplish blocking ambient radiation at the shield that, if allowed to reach the eyes of the subject, would interfere with the light therapy provided to the subject by the radiation emitted between the eyes of the subject and the shield, and enabling ambient radiation to pass through the shield that does not interfere with the light therapy provided to the subject by the radiation emitted between the eyes of the subject and the shield, wherein interfering with the light therapy includes reducing the impact of the light therapy on the circadian rhythms and/or light deficient disorders of the subject, wherein ambient radiation having third wavelengths reduces the impact of the light therapy on the circadian rhythms and/or light deficient disorders of the subject during the first portion of light therapy and does not reduce the impact of the light therapy on the circadian rhythms and/or light deficient disorders of the subject during the second portion of light therapy, and wherein, based on the predetermined light therapy algorithm, the ambient radiation having third wavelengths is blocked during the first portion of light therapy and enabled to pass through the one or more apertures during the second portion of the light therapy.

13. The method of claim 12, wherein controlling the transmission characteristics of the one or more filters comprises varying the transmission of the one or more filters for radiation within a predetermined wavelength range.

14. The method of claim 12, wherein controlling the transmission characteristics of the one or more filters comprises varying the transmission of the one or more filters for radiation across the visible spectrum.

15. A mask configured to provide light therapy to a subject to impact circadian rhythms and/or light deficient disorders of the subject, the mask comprising:

means for covering the eyes of a subject such that ambient radiation is blocked from the eyes of the subject, the means for covering having one or more apertures configured to allow ambient light to reach the eyes of the subject;

means for emitting radiation between the eyes of the subject and the means for covering that provides light therapy to the subject, emitting radiation that provides light therapy including emitting radiation having first wavelengths during a first portion of the light therapy and emitting radiation having second wavelengths during a second portion of the light therapy;

means for blocking ambient radiation, at the one or more apertures in the means for covering, having wavelengths that, if allowed to reach the eyes of the subject, would interfere with the light therapy provided to the subject by the radiation emitted between the eyes of the subject and the means for covering; and means for enabling ambient radiation to pass through the one or more apertures in the means for covering at wavelengths that do not interfere with the light therapy provided to the subject by the radiation emitted between the eyes of the subject and the means for covering, wherein interfering with the light therapy includes reducing the impact of the light therapy on the circadian rhythms and/or light deficient disorders of the subject, wherein ambient radiation having third wavelengths reduces the impact of the light therapy on the circadian rhythms and/or light deficient disorders of the subject during the first portion of light therapy and does not reduce the impact of the light therapy on the circadian rhythms and/or light deficient disorders of the subject during the second portion of light therapy, and wherein the ambient radiation having third wavelengths is blocked by the means for blocking during the first portion of light therapy and enabled to pass by the means for enabling through the one or more apertures during the second portion of the light therapy.

16. The mask of claim 15, wherein the means for blocking ambient radiation at the one or more apertures in the means for covering that, if allowed to reach the eyes of the subject, would interfere with the light therapy provided to the subject by the radiation emitted between the eyes of the subject and the means for covering comprises means for blocking ambient radiation at wavelengths across the visible spectrum that, if allowed to reach the eyes of the subject, would interfere with the light therapy provided to the subject by the radiation emitted between the eyes of the subject and the means for covering, and wherein the means for enabling ambient radiation to pass through the one or more apertures in the means for covering that does not interfere with the light therapy provided to the subject by the radiation emitted between the eyes of the subject and the means for covering comprises means for enabling ambient radiation to pass through the means for covering at wavelengths across the visible spectrum that do not interfere with the light therapy provided to the subject by the radiation emitted between the eyes of the subject and the means for covering.

17. The mask of claim 15, wherein ambient radiation that, if allowed to reach the eyes of the subject, would interfere with the light therapy provided to the subject by the radiation emitted between the eyes of the subject and the means for covering comprises ambient radiation having a wavelength at or above about 580 nm, and wherein ambient radiation that does not interfere with the light therapy provided to the subject by the radiation emitted between the eyes of the subject and the means for covering comprises ambient radiation having a wavelength at or below about 580 nm.

18. The mask of claim 15, further comprising means for controlling the emission of radiation between the means for covering and the eyes of the subject, the means for blocking, and the means for enabling in accordance with a predetermined light therapy algorithm.

19. A mask configured to provide light therapy to a subject to impact circadian rhythms and/or light deficient disorder of the subject, the mask comprising:

means for covering the eyes of a subject such that ambient radiation is blocked from the eyes of the subject, the means for covering having one or more apertures configured to allow ambient light to reach the eyes of the subject;

means for emitting radiation between the eyes of the subject and the means for covering that provides light therapy to the subject, emitting radiation that provides light therapy including emitting radiation having first wavelengths during a first portion of the light therapy and emitting radiation having second wavelengths during a second portion of the light therapy;

means for blocking ambient radiation, at the one or more apertures in the means for covering, having wavelengths that, if allowed to reach the eyes of the subject, would interfere with the light therapy provided to the subject by the radiation emitted between the eyes of the subject and the means for covering; and means for enabling ambient radiation to pass through the one or more apertures in the means for covering having wavelengths that do not interfere with the light therapy provided to the subject by the radiation emitted between the eyes of the subject and the means for covering;

means for controlling the emission of radiation between the means for covering and the eyes of the subject in accordance with a predetermined light therapy algorithm; and means for controlling transmission characteristics of the means for blocking and the means for enabling in accordance with the predetermined light therapy algorithm to accomplish the blocking and the enabling wherein interfering with the light therapy includes reducing the impact of the light therapy on the circadian rhythms and/or light deficient disorders of the subject, wherein ambient radiation having third wavelengths reduces the impact of the light therapy on the circadian rhythms and/or light deficient disorders of the subject during the first portion of light therapy and does not reduce the impact of the light therapy on the circadian rhythms and/or light deficient disorders of the subject during the second portion of light therapy, and wherein, based on the light therapy algorithm, the ambient radiation having third wavelengths is blocked by the means for blocking during the first portion of light therapy and enabled to pass by the means for enabling through the one or more apertures during the second portion of the light therapy.

20. The mask of claim 19, wherein the means for controlling the transmission characteristics comprises means for varying transmission characteristics of one or more filters for radiation within a predetermined wavelength range.

21. The mask of claim 19, wherein the means for controlling the transmission characteristics comprises means for varying transmission characteristics of one or more filters for radiation across the visible spectrum.

* * * * *